United States Patent [19]

Kimura et al.

[11] Patent Number: 5,130,243
[45] Date of Patent: Jul. 14, 1992

[54] PROCESS FOR PRODUCTION OF STARCH SUGAR

[75] Inventors: Takashi Kimura, Yokohama; Masafumi Ogata, Kawasaki; Masaaki Noguchi, Mitaka; Teruo Nakakuki, Mishima; Masahiro Yoshida; Taizo Miwa, both of Fuji, all of Japan

[73] Assignees: Nihon Shokuhin Kako Co., Ltd., Tokyo; Chiyoda Chemical Entineering & Constructions Co., Ltd., Yokohama, both of Japan

[21] Appl. No.: 494,851

[22] Filed: Mar. 15, 1990

Related U.S. Application Data

[63] Continuation of Ser. No. 86,527, Aug. 17, 1987, abandoned.

[30] Foreign Application Priority Data

Aug. 28, 1986 [JP] Japan .................. 61-200046
Sep. 19, 1986 [JP] Japan .................. 61-219430
Oct. 13, 1986 [JP] Japan .................. 61-242730

[51] Int. Cl.$^5$ .................. C12P 19/22; C12P 19/20; C12P 19/16; C12N 11/12

[52] U.S. Cl. .................. 435/95; 435/96; 435/98; 435/99; 435/179; 435/201; 435/205; 435/210

[58] Field of Search .................. 435/95, 96, 98, 99, 435/179, 201, 205, 210

[56] References Cited

U.S. PATENT DOCUMENTS

| | | | |
|---|---|---|---|
| 4,011,137 | 3/1977 | Thompson et al. | 195/31 R |
| 4,102,745 | 7/1978 | Thompson et al. | 195/31 R |
| 4,167,447 | 9/1979 | Masri et al. | 435/178 |
| 4,338,398 | 7/1982 | Yoneyama | 435/95 |
| 4,511,654 | 4/1985 | Rohrbach et al. | 435/95 |

*Primary Examiner*—Charles L. Patterson, Jr.
*Attorney, Agent, or Firm*—Frishauf, Holtz, Goodman & Woodward

[57] ABSTRACT

Process for producing starch sugar which comprises contacting liquefied starch with amylase immobilized onto porous chitosan. Immobilized debranching enzyme can be used in combination with the amylase. The debranching enzyme is immobilized onto a specific support.

6 Claims, 3 Drawing Sheets

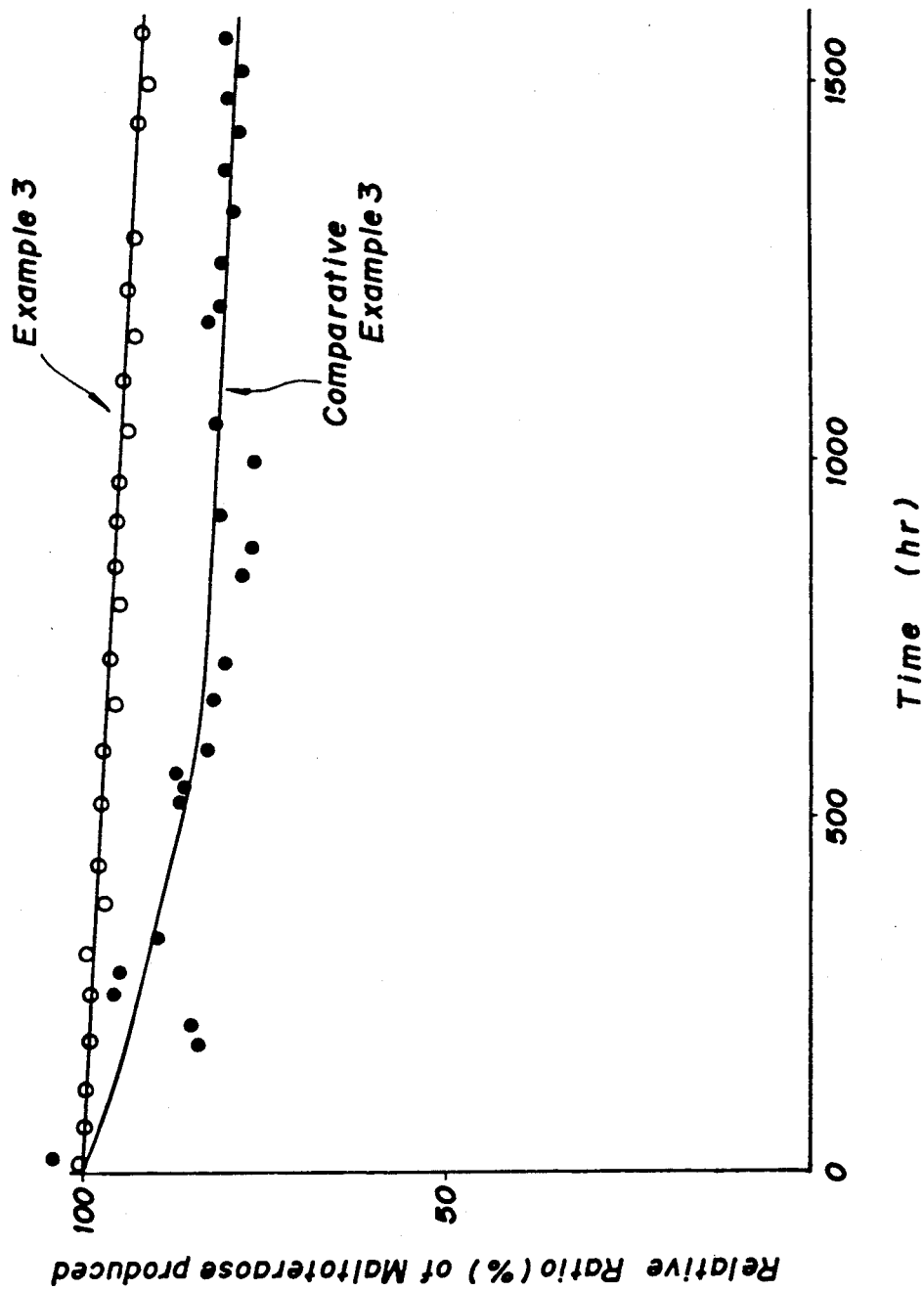

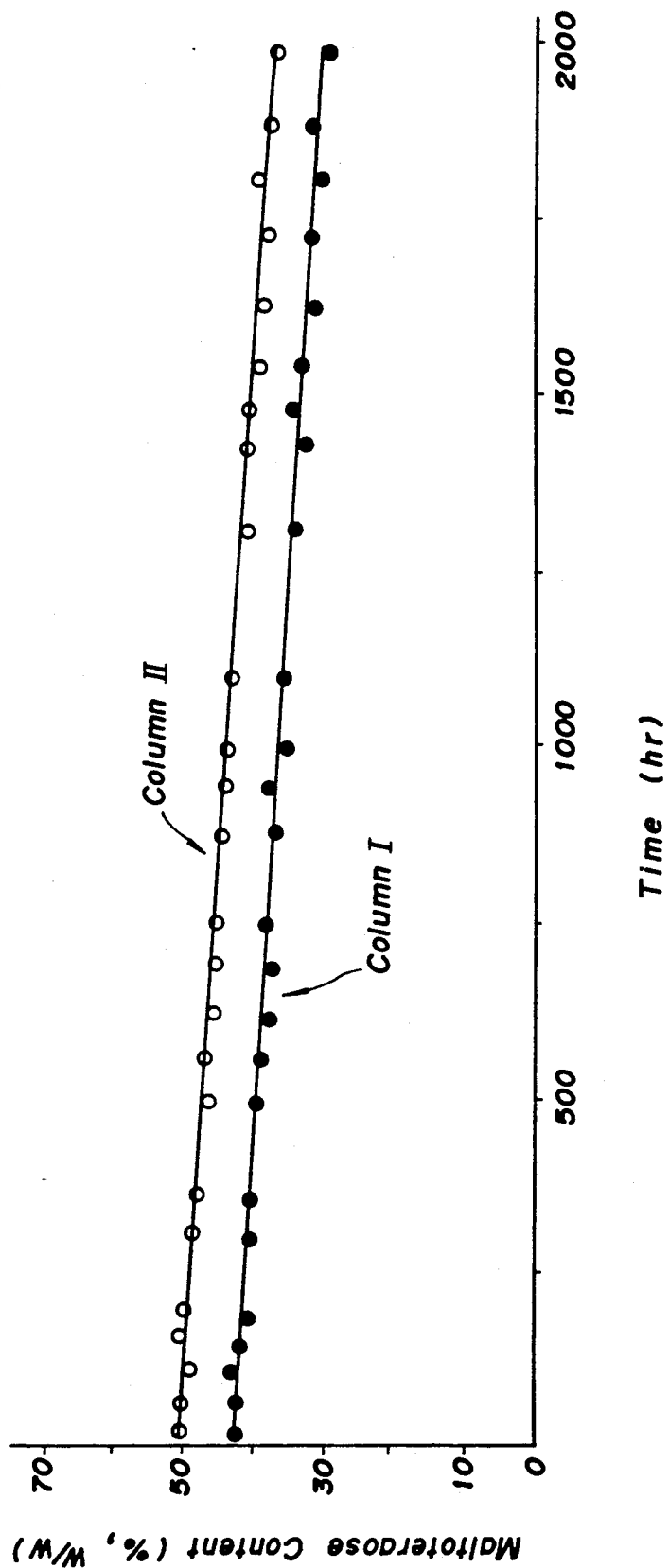

PROCESS FOR PRODUCTION OF STARCH SUGAR

This application is a continuation of application Ser. No. 07/086,527, filed Aug. 17, 1987.

BACKGROUND OF THE INVENTION

The present invention relates to a process for production of starch sugar and more particularly to a process for production of starch sugar which comprises introducing liquefied starch into a reactor filled with various amylases immobilized onto porous chitosan, to thereby convert the starch into the corresponding starch sugar such as glucose, maltose and maltooligosaccharides.

Furthermore the present invention relates to immobilized debranching enzyme and more particularly to debranching enzyme immobilized onto a specific support which is to be used in the production of various starch sugars. This debranching enzyme, when used in combination with various immobilized amylases, permits production in high yield of starch sugar such as glucose, maltose and maltooligosaccharides from liquefied starch.

Various methods for producing starch sugar utilizing immobilized enzyme have been proposed. For example, a method for producing a high concentration of glucose, employing immobilized glucoamylase is disclosed in Japanese Patent Publication No. 17517/1982, Japanese Patent Application Laid-Open No. 60989/1983, etc. The method disclosed in Japanese Patent Publication No. 17517/1982, however, has a disadvantage in that the concentration of glucose is insufficiently low. In accordance with the method disclosed in Japanese Patent Application Laid-Open No. 60989/1983, a high concentration of glucose can be produced from potato starch as the starting material. However, there is no description about the use as the starting material of corn starch and the like from which a high concentration of glucose is generally difficult to produce.

Immobilization of $\beta$-amylase and production of maltose employing the immobilized $\beta$-amylase are disclosed in Japanese Patent Application Laid-Open No. 198977/1984, etc. In this immobilized $\beta$-amylase, it is desired to more improve the stability of enzyme activity The present inventors have developed a method for producing maltooligosaccharide by immobilizing amylase which is able to produce maltooligosaccharide having a higher degree of polymerization than maltose Although this method is sufficiently suitable for practical use, it is desirable to more efficiently utilize expensive enzyme.

As a result of extensive investigations on a support on which amylase is immobilized, it has been found that the liquid flow rate can be increased in comparison with the prior art method and further that enzyme activity can be improved more stably. It has further been found that the yield of the desired starch sugar can be increased by employing a dual enzyme system including two kinds of immobilized enzymes in combination.

SUMMARY OF THE INVENTION

The present invention provides a process for production of starch sugar which comprises contacting liquefied starch with amylase immobilized onto porous chitosan.

Moreover the present invention provides a process for production of starch sugar which comprises contacting liquefied starch with amylase immobilized onto porous chitosan as well as with immobilized debranching enzyme.

A further aspect of the present invention relates to a debranching enzyme immobilized on selected special supports.

BRIEF DESCRIPTION OF THE DRAWINGS

FIG. 2 is a graph showing changes with time of the maltotetraose content of the reaction solution in Example 3 and Comparative Example 3.

FIG. 3 is a graph comparing the amount of maltotetraose formed in the single enzyme system (Column 1) with that in the dual enzyme system (Column II) when the liquid was passed through continuously.

DETAILED DESCRIPTION OF THE INVENTION

Figure 1:
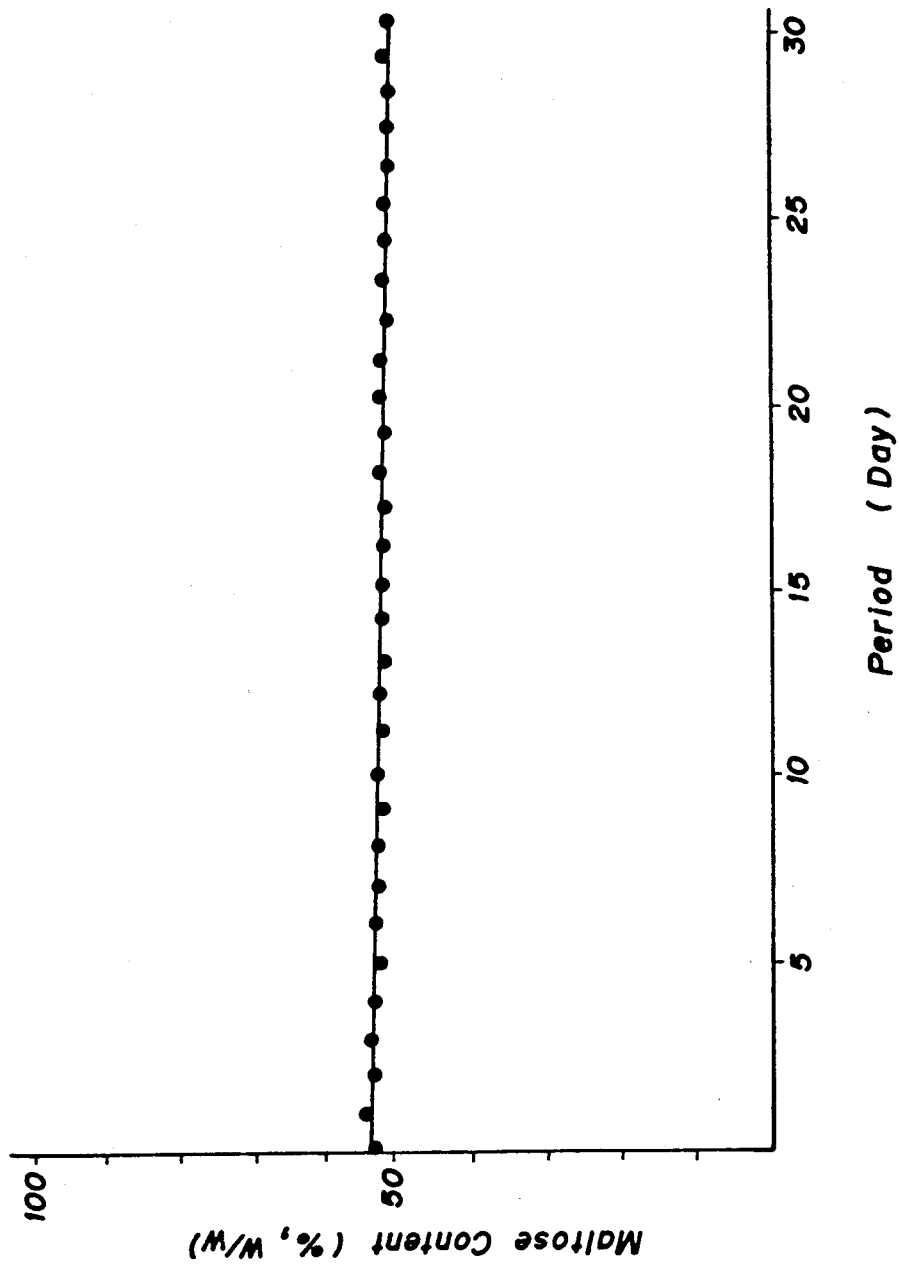
FIG. 1 is a graph showing changes with time of the maltose content of the reaction solution in Example 2.

Various types of amylases can be used in the present invention. As glucoamylase, those originating from fungi belonging to genera of *Rhizopus, Apergillus, Mucor* and *Piricularia*, etc. are mainly used. Particularly suitable is amylase originating from *Rhizopus delemar.* In addition, those originating from yeasts belonging to genera of *Endomyces, Trichoderma* and *Saccharomyces* and from bacteria such as *Clostridium acetobutyricum* are known. $\beta$-Amylase includes, as well as the one originating from plant such as soybean and malt, one originating from microorganisms such as *Bacillus polymyxa* (D. French; Arch. Biochem. Biophys., 104, 338 (1964)), *Bacillus cereus* (Y. Takasaki, Agric. Biol. Chem., 40, 1515, 1523 (1976)), bacteria belonging to genus *Pseudomonas* (S. Sinke et al., J. Ferment. Technol., 53, 693, 698 (1975)), *Streptomyces hygroscopicus* (Y. Hidaka et al., Starke, 26, 413 (1974)) and *Streptomyces praecox* (K. Wako et al., Denpun Kagaku (The Japanese Soc. of Starch Sci.), 25, 155 (1978)).

As amylase forming oligosaccharide having a higher degree of polymerization than maltose, the following are known.

Maltotriose-forming amylase (originating from *Streptomyces griseus* (K. Wako et al., Denpun Kagaku (The Japanese Soc. of Starch Sci.), 26, 175 (1979)), and genus *Bacillus sp.* (Y. Takasaki, Abstract Paper of the Annual Meeting of the Agricultural Chemical Society of Japan, p. 169 (1983)).

Maltotetraose-forming amylase (originating from *Pseudomonas stutzeri* (J.F. Bobyt and R.J. Ackerman, Arch. Biochem. Biophys., 145, 105 (1971)).

Maltopentaose-forming amylase (originating from *Bacillus licheniformis* (N. Saito, Arch. Biochem. Biophys., 155, 290 (1973)), S. Kobayashi et al., Abstract Paper of the Annual Meeting of the Japanese Soc. of Starch Sci p. 301 (1983), and N. Yoshigi et al., Abstract paper of the Annual Meeting of the Agricultural Chemical Society of Japan, p. 584 (1984)).

Maltohexaose-forming amylase (originating from *Aerobacter aerogenes* (K. Kainuma et al., FEBS Lett., 26 281 (1972), J.F. Kennedy and C.A. White, Starke, 31, 93 (1979) and H. Taniguchi et al., Denpun Kagaku (The Japanese Soc. of Starch Sci.), 29, 107 (1982), and Y. Takasaki, Agric. Biol. Chem., 47, 2193 (1983)).

Chitosan to be used as a support for immobilization of the above amylase is obtained by deacetylating natural polymer chitin which is widely present in the world of nature, especially in *Crustacea, Arthropods*, etc. Particularly preferred is chitosan which is granulated and made porous, or which is provided with good adsorption capability. For example, chitosan sold under the trade name of Chitopearl, (produced by Fuji Spinning Co., Ltd.) is suitable. This chitosan is produced by deacetylating natural polymer chitin and cross-linking with dicarboxylic acid, dialdehyde, diisocyanate, etc. to impart acid resistance and further by introducing an aliphatic or aromatic functional group as the spacer, and is in the form of porous beads and is excellent in pH stability, chemical resistance and thermal stability. This "chitopearl" has a particle diameter of 0.1 to 3.0 mm, a pore diameter of not more than 3.0 μm, and a specific surface area of 15 to 230 m2/g, although the present invention is not limited by these values.

It has further been found that by using immobilized maltooligosaccharide-forming amylase in combination with immobilized debranching enzyme, high purity maltooligosaccharide can be produced more efficiently and furthermore the column operation can be carried out in a wide range of the flow rate, especially at a high flow rate in comparison with the case of using a single system of immobilized maltooligosaccharide-forming amylase.

Immobilization of amylase onto chitosan can be carried out by any desired techniques such as a method in which amylase and chitosan are contacted in a buffer solution. For example, 100 mg of Chitopearl is sufficiently equilibrated with a 0.01 to 0.20 M concentration of buffer (pH: 4.0-8.0), and then 5 to 500 units of amylase dissolved in 2 ml of a buffer is added and sufficiently mixed therewith. The resulting mixture is allowed to stand at room temperature for 0.5 to 24 hours or is subjected to reciprocal shaker (120 strokes/ minute) for a period of 0.5 to 5.0 hours and then filtered with a glass filter. The residue is washed with 50 ml of a buffer.

For the immobilized enzyme thus obtained, the apparent degree of immobilization is not less than 90% and the exhibited activity is 40 to 2,000 units per gram of the wet support. The apparent degree of immobilization is a value calculated from the following equation:

$$\frac{\text{Activity of Enzyme Supplied} - \text{Activity of Enzyme in Washing Solution}}{\text{Activity of Enzyme Supplied}} \times 100(\%)$$

For immobilization of enzyme, as well as the above method, a method can be employed in which the support is charged in a column and an enzyme solution is passed through the column by the up-flow or down-flow method In the immobilized amylase to be used in the present invention, the immobilization can be carried out very easily and furthermore the exhibited activity of the immobilized enzyme is sufficiently high for practical use.

The immobilized debranching enzyme to be used in the second invention will hereinafter be explained.

Debranching enzymes which can be used in the present invention include pullulanase originating from microorganisms such as *Bacillus acidopullulyticus* and *Klebsiella pueumoniae*, and isoamyalse produced by *Pseudomonas amyloderamosa* and microorganisms belonging to genus *Cytophaga*. Almost all of glucose-forming amylases have the optimum pH in the range of 4.0 to 6.0, and almost all of maltooligosaccharideforming amylases have the optimum pH in the range of 5.0 to 8.5. It is desirable, therefore, to use debranching enzymes having the same stable and optimum pH range as above.

With regard to the support to be used in immobilization of the debranching enzyme, any support can be used as long as it exhibits high exhibited activity by immobilization. The following supports are particularly preferred to use. As a result of the present inventors' investigations to choose supports which are able to immobilize various debranching enzymes with high efficiency, it has been found that slightly weak acidic porous adsorption resins, weakly acidic cationic resins, phenol-based adsorption resins, granular porous chitosan and so on are particularly suitable as the support. Representative examples include Duolite resins produced by Diamond Shamrock Corp. and sold under the trade names of S-761, S-762, ES-771, C-464, A-7, S-587 and A-562, and the above described Chitopearl.

A method of immobilization of the debranching enzyme is not critical; for example, the methods as described above can be applied. In more detail, a method can be employed in which the enzyme and the support are brought into contact in a buffer. For example, 100 mg of Chitopearl is sufficiently equilibrated with a 0.01 to 0.20 M buffer (pH: 4.0-8.0), and then 5 to 500 units of debranching enzyme dissolved in 2 ml of buffer is added and sufficiently mixed. The resulting mixture is allowed to stand at room temperature for 0.5 to 24 hours or is subjected to reciprocal shaker (120 strokes/minute) for 0.5 to 5.0 hours, and then filtered with a glass filter and washed with 50 ml of various buffers.

For the immobilized enzyme thus obtained, the apparent immobilization ratio is not less than 90% and the exhibited activity of the immobilized enzyme is 40 to 2,000 units per gram of the wet weight of the support The apparent immobilization ratio is a value as calculated from the following equation:

$$\frac{\text{Activity of Enzyme Supplied} - \text{Activity of Enzyme in Washing Solution}}{\text{Activity of Enzyme Supplied}} \times 100(\%)$$

For the immobilization of the enzyme, as well as the method as described above, a method can be applied in which the support is charged in a column and the enzyme solution is passed through the column by the down-flow or up-flow method.

The activities of the native debranching enzyme and of the immobilized debranching enzyme can be determined by using pullulan or amylopectin (glutinous rice starch) as a substrate and reacting it under the optimum reaction conditions. The enzyme activity is indicated in terms of the amount of enzyme to hydrolyze 1 μmol of α-1,6-glucoside bond for one minute under the reaction conditions, as one unit (1 International Unit (IU)).

The immobilized debranching enzyme is used in combination with amylase such as native or immobilized glucoamylase, β-amylase or maltooligosaccharide-producing amylase usually for the purpose of increasing the yield of starch sugar respectively produced.

That is, if the immobilized debranching enzyme is used in combination with glucoamylase, when the glucose purity is not less than 90% the yield can be increased by 1 to 3%. Even in a case where the immobilized debranching enzyme and immobilized glucose amylase are used in combination, the glucose purity exceeding 95% can be obtained If the immobilized debranching enzyme is used in combination with β-amylase, when the maltose purity is not less than 50%, the yield can be increased by 5 to 15%.

If the immobilized debranching enzyme is used in combination with maltooligosaccharide-forming amylase, when the maltooligosaccharide purity is not less than 30%, the yield can be increased by about 3 to 8%.

As the starch to be used in the process of the present invention, various ones can be used. Usually, potato starch, sweet potato starch, corn starch, waxy corn starch, cassava starch and so forth are used. The dextrose equivalent (DE) of liquefied starch to be passed through the reactor is usually 1 to 35 and preferably 5 to 20. When DE of the liquefied starch is not more than 1 in the case of waxy corn starch, and not more than 5 in the case of other starches, retrogradation occurs seriously and thus care must be taken in handling them. On the other hand, if DE is more than 35, in the case of glucose formation the reverse synthesis is accelerated by flucoamylase, and thus the amounts of isomaltose, panose and so on are increased, resulting in a decrease in the yield of glucose. Furthermore, the amounts of low molecular saccharide such as glucose and maltose being produced is increased in comparison with the amount of maltooligosaccharide produced, and the yield of maltooligosaccharide is decreased. A method of liquefying the starch is not critical; usually the starch is liquefied by treating with bacterial liquefying α-amylase or acid such as hydrochloric acid. The maltooligosacchadie includes maltose, maltotriose, maltotetraose, maltopentaose, maltohexaose and so forth.

As a result of the present investigations on conditions to efficiently produce various starch sugars by the use of immobilized enzyme, it has been found that the factors as described below exert great influences. The factors include the type and concentration of the substrate, the amount of the substrate supplied, the type of the support for immobilization (physical properties), the amount of the enzyme immobilized, the amount of the immobilized enzyme to be charged in the column, the temperature of the reaction system, pH and so forth.

It has between found that only if the above factors are controlled within the ranges as described hereinafter, starch sugar can be produced efficiently. That is, in accordance with the method of the present invention, various types of starch sugars can be produced efficiently by charging the immobilized amylase to the reactor and feeding the liquefied starch as described above to the reactor under the conditions that the weight hourly space velocity per unit activity of the immobilized enzyme is $1\times10^{-4}$ to $2\times10^{-1}$ hr$^{-1}$ (IU/g)$^{-1}$. More preferably, the conditions of $1\times10^{-4}$ to $3\times10^{-3}$ hr$^{-1}$ (IU/g)$^{-1}$ for glyucoamylase, $1\times10^{-4}$ to $4\times10^{-3}$ hr$^{-1}$ (IU/g)$^{-1}$ for β-amylase, and $3\times10^{-4}$ to $2\times10^{-1}$ hr$^{-1}$ (IU/g)$^{-1}$ for various maltooligosaccharideproducing amylase should be applied. The weight hourly space velocity per unit activity of the immobilized enzyme is a value as determined by the method as described below.

The same immobilized amylase (10 mg-wet base) as the one to be charged to the reactor is added to 0.5 ml of 10 mM buffer (pH 7.0) in a 50 ml Erlenmeyer flask. Then 5.0 ml of the same substrate as the one to be supplied to the reactor (identical with respect to the type and concentration of the starch, etc. as well) is added. The enzymatic reaction is carried out at the same temperature as in the reactor (usually at 40° C.) while reciprocating for 10 minutes under conditions of 120 strokes/min and 4 cam width by the use of a reciprocating shaker. The exhibited activity is determined by measuring the formed reducing sugar, which is measured by the SomogyiNelson method, or directly with an analytical apparatus such as high performance liquid chromatography (this exhibited activity is referred to "A IU/g-support"). The enzyme activity is equivalent to the amount of enzyme to hydrolyze 1 μmol of glycoside bond for one minute under the respective reaction conditions as one unit (International Unit (IU)). The weight hourly space velocity per unit activity is calculated from the following equation:

$$C/(A\times B)\mathrm{hr}^{-1}(\mathrm{IU}/g)^{-1}$$

where B is the amount of the immobilized enzyme to be supplied to the reactor (g (wet)), and C is the amount (as dry solid) of the liquefied starch to be supplied to the reactor (g/hr). When DE is large, the starting material contains the objective starch sugar and smaller sugars than the objective one. It is more practical, therefore, that as the above C value, the amount of the dry solid excluding the above starch sugar and other sugars is employed. If the weight hourly space velocity per unit activity is more than $2\times10^{-1}$ hr$^{-1}$(IU/g)$^{-1}$, in detail more than $3\times10^{-3}$ hr$^{-1}$(IU/g)$^{-1}$ in the case of glucoamylase, more than $4\times10^{-3}$ hr$^{-1}$(IU/g)$^{-1}$ in the case of β-amylase, or more than $2\times10^{-1}$ hr$^{-1}$(IU/g)$^{-1}$ in the case of amylase producing maltooligosaccharide having a higher degree of polymerization than maltotriose, that is, the reaction time in the reactor is short, the hydrolysis reaction proceeds only insufficiency and thus the yield of the specific starch sugar is undesirably decreased. In the production of maltooligosaccharide, if the weight hourly space velocity per unit activity is smaller than $1\times10^{-4}$ hr$^{-1}$ (IU/g)$^{-1}$, that is, the reaction time in the reactor is too long, the maltooligosaccharide formed undergoes excessive degradation as described in the references as described hereinafter. As a result, sugar having a low molecular weight, such as glucose and maltose, is formed and thus not only the purity of the product is seriously decreased but also the efficiency in the subsequent purification and separation is reduced.

When regard to excessive decomposition of maltooligosaccharide having a higher degree of polymerization than maltose, it is described in T. Nakakuki et al., Carbohydr. Res., 128, 297 (1984) that maltooligosaccharide-forming amylase specifically produces the respective oligosaccharide (e.g., maltotriose, maltotetraose, maltopentaose and maltohexaose) at an earier stage of the reaction, but at the later stage of the reaction, decompose the product itself.

In the case of glucoamylase, when the weight hourly space velocity per unit activity becames below $1\times10^{-3}$ hr$^{-1}$ (IU/g)$^{-1}$, the reverse reaction forming panose and isomaltose proceeds, decreasing the yield of the objective glucose.

In practice, however, if the weight hourly space velocity per unit activity is less than $1\times10^{-4}$ hr$^{-1}$(IU/g)$^{-1}$, the residence time in the reactor is too long an the size of the reactor is inevitably increased. This is unsuitable from an economic standpoint, and at the same time the objective starch sugar is decrease as a result of retrogradation of the liquefied starch, which may cause operation trouble.

In accordance with the present invention using the immobilized amylase, the reaction conditions can be expected to extend in comparison with the case that the native amylase which is not immobilized is used. For example, in the case of maltotetraose-forming amylase immobilized onto chitosan, the temperature stability is extended by about 10° C. to the higher temperature side and at the same time, the pH stability is improved over a wide range. It has further been found that the immobilization treatment raises the optimum temperature by 10-15° C. and extends the optimum pH curve to the acidic side. The enzymatic properties of the immobilized enzyme are considerably improved. Thus, in comparison with the case that the native enzyme is used, the reaction can be carried out under greatly advantageous conditions.

In production of maltooligosaccharide, for example, by the method of the present invention, various purification processes can be employed depending on the objective purity of maltooligosaccharide. For example, maltooligosaccharide having a purity of about 20 to 60% can be obtained by feeding 20–40% (w/w) of liquefied starch to a reactor charged with the above immobilized maltooligosaccharide-forming amylase, under conditions as described above. Maltooligosaccharide having a higher purity (60 to 100%) can be obtained by subjecting the reaction product from the reactor to further purification and separation. For this purification/separation process, various methods can be employed. For example, membrane ultrafiltration chromatography, gel filtration chromatograph, cation exchange resin column chromatography and carbon column chromatogrpahy are effective. The yield of maltoogligosaccharide per the liquefied starch can be increased by recycling part or all of the undecomposition product obtained in the above purification/separation process, to the reactor charged with the immobilized maltooligosaccharide-forming enzyme as part of the starting material to be fed. Moreover, a part or all of the undecomposed product can be used as it si as limit dextrin.

The second invention using the immobilized amylase in combination with the immobilized debranching enzyme will hereinafter be explained.

With regard to the ratio of the immobilized enzyme to the immobilized debranching enzyme, as the amount of the immobilized debranching enzyme is more increased, the concentration (yield) of starch sugar can be more increased. The ratio of the immobilized amylase to the immobilized debranching enzyme is usually 0.1/1 to 5/1 and preferably 0.2/1 to 2/1 exhibited activity base). Even if the ratio is increased to more than the above upper limit, no additional effect can be obtained and the size of the reactor is increased correspondingly, which is unsuitable from an economic standpoint. Therefore, the weight hourly space velocity per unit activity in the case of using the debranching enzyme in combination is determined taking into consideration only the exhibited activity of amylase but not the exhibited activity of the debranching enzyme as the exhibited activity (A IU/g) in the above equation.

In a case where both enzymes are used in combination, the charging method can take various embodiments. For example, a method in which the two immobilized enzymes are charged to separate containers, a method in which the two enzymes are mixed and then charged to the same container, a method in which two native enzymes are mixed in a given ratio and immobilized at the same time, and then charged to the container, and so forth can be employed.

In accordance with the method of the present invention, in production of glucose, maltose and further maltooligosaccharide having a higher degree of polymerization than maltose, the weight hourly space velocity per unit activity of the immobilized enzyme can be increased in comparison with the prior art method and furthermore the enzyme activity can be kept stable for a long time. For this reason, the objective starch sugar can be produced with good efficiency and further in high yield. In particular, if the immobilized dual enzyme system using amylase in combination with debranching enzyme is used, the yield of the objective substance is greatly increased.

Even when corn starch is used as the staring material, a high concentration of starch sugar (especially in the case of glucose production) can be obtained, which is equal to that of native enzyme.

The present invention is described in greater detail with reference to the following examples.

EXAMPLE 1

Glucoamylase originating from *Rhizopus delemar* (produced by Shin Nippon Kagaku Co., Ltd.) was immobilized onto porous chitasan (trade name: Chitopearl BCW 3505, produced by Fuji Spinning Co., Ltd.) as the support. That is, chitosan as the support was sufficiently equilibrated with a 20 a mM acetate buffer (pH 5.5), 10 g (wet) of the chitosan support was placed in a 100 ml Erlenmeyer flask, and then glucoamylase was added in an amount of 1,050 units per gram of the support (volume: 10 ml). The resulting mixture was subjected to reciprocal shaker (120 strokes/minute) at room temperature for 1 hour to immobilize glucoamylase. The enzyme was sufficiently washed with a 20 mM acetate buffer (pH 5.0) until no protein was eluted, to obtain an immobilized glucoamylase sample. This sample was measured for exhibited activity by the method as described above, and it was found to be 435 IU/g-support.

Then 1 ml of the immobilized glucoamylase was charged to a glass column (diameter: 10 mm; length: 20 mm), and a 30% (w/w) liquefied corn starch (DE=11, pH 5.5) as the substrate was continuously passed through the above glass column at a temperature of 50° C. and a space velocity of 0.25, 0.5 or 1.0 hr$^{-1}$ (the weight hourly space velocity per unit activity was $2.48 \times 10^{-4}$, $4.95 \times 10^{-4}$ or $9.89 \times 10^{-3}$ hr$^{-1}$ (IU/g)$^{-1}$, respectively.). The space velocity was calculated by the following equation:

$$\text{Space Velocity (hr}^{-1}) = \frac{\text{Flow Rate (ml/hr)}}{\text{Bed Volume (ml)}}$$

The results are shown in Table 1.

COMPARATIVE EXAMPLE 1

The procedure of Example 1 was repeated with the exception that a pour weakly basic anion exchange resin, Duolite A-7 (produced by Diamond Shamrock Corp.) was used as the support and immobilization was performed by the method described in Example 1 of Japanese Patent Application Laid-Open No. 60989/1983. The exhibited activity of the immobilized enzyme was 157 IU/g-support. The same testing as in Example 1 was performed using the immobilized enzyme (the weight hourly space velocity per unit activity was $6.85 \times 10^{-4}$, $1.37 \times 10^{-3}$ or $2.74 \times 10^{-3}$ hr$^{-1}$ (IU/g)$^{-1}$.). The results are shown in Table 1.

TABLE 1

| | Concentration of Glucose in Reaction Mixture (%) | |
|---|---|---|
| Space Velocity (hr$^{-1}$) | Example 1 | Comparative Example 1 |
| 0.25 | 95.2 | 94.2 |
| 0.5 | 96.7 | 93.8 |
| 1.0 | 95.2 | 87.4 |

EXAMPLE 2

Porous chitosan (trade name: Chitopearl BCW 3505, produced by Fuji Spinning Co., Ltd.) was used as the support, and β-maylase originating from soybean, produced by Nagase Seikagaku Kogyo Co., Ltd.) was immobilized thereto by the usual method. The exhibited activity of the immobilized β-amylase as obtained above was 230 IU/g-support.

This immobilized β-amylase was charged to a glass column diameter: 27 mm; length: 130 mm), and a 25% (w/w) liquefied starch (DE=7, pH 6.0) was used as the substrate and continuously passed through the glass column at a temperature of 50° C. and a space velocity of 0.2, 0.5, 1.0 or 1.5 hr$^{-1}$ (the weight hourly space velocity per unit activity was $3.09 \times 10^{-3}$, $7.73 \times 10^{-4}$, $1.55 \times 10^{-3}$ or $2.32 \times 10^{-3}$ hr$^{-1}$(IU/g)$^{-1}$, respectively). The results are shown in Table 2. Changes in the maltose content of the reaction mixture with a elapsed time when the substrate was continuously passed through the column at a space velocity of 1.5 hr$^{-1}$ are shown in FIG. 1.

COMPARATIVE EXAMPLE 2

Duolite adsorption resin S-761 (produced by Diamond Shamrock Corp.) was used as the support, and β-amylase wa immobilized thereto the in same manner as in Example 1. The exhibited activity of the immobilized β-amylase was 198 IU/g-support.

Then 10 ml of the above immobilized enzyme was charged to a glass column in the same manner as in Example 2, and a 25% (w/w) liquefied starch (DE=7, pH 6.0) as the substrate was continuously passed through the glass column at a temperature of 50° C. and a space velocity of 0.2, 0.5, 1.0 or 1.5 hr$^{-1}$ (the weight hourly space velocity per unit activity was $3.59 \times 10^{-4}$, $8.98 \times 10^{-3}$, $1.80 \times 10^{-3}$ or $2.70 \times 10^{-3}$ hr$^{-1}$ (IU/g)$^{-1}$, respectively.). The results are shown in Table 2.

TABLE 2

| | Concentration of Maltose in Reaction Mixture (%) | |
|---|---|---|
| Space Velocity (hr$^{-1}$) | Example 2 | Comparative Example 2 |
| 0.2 | 52.5 | 52.4 |
| 0.5 | 52.5 | 44.8 |
| 1.0 | 52.3 | 37.5 |
| 1.5 | 52.1 | 30.3 |

It is apparent from Table 2 and FIG. 1 that in accordance with the present invention, a large amount of maltose can be obtained at a higher space velocity than in the case of using the prior art immobilized enzyme, and that even after 30 days, almost no reduction in activity is observed an the half-life is more than one year.

EXAMPLE 3

Maltotetraose-forming amylase (originating from *Pseudomonas stutzeri*, specific activity 80.0 IU/mg-protein) was used as the enzyme and immobilized onto chitosan beads (trade name: Chitopearl BCW 3505, produced by Fuji Spinning Co., Ltd.) as the immobilization support to obtain an immobilized enzyme. That is, 20 g of the support was equilibrated with a 50 mM Tris-HCl buffer (pH 7.0), and 20,000 IU of the enzyme dissolved in 100 ml of the same buffer as used above was added thereto. The resulting mixture was subjected to reciprocal shaker (120 strokes/minute and 4 cm width in a 300 ml Erlenmeyer flask) to immobilize the enzyme onto the support. Then, after filtration with a filter paper, the enzyme was fully washed with a 10 mM Tris-HCl buffer (pH 7.0) until no protein was eluted, to obtain an immobilized maltotetraose-forming amylase having an exhibited activity of 350 IU/g-protein.

Then 10 ml of the maltotetraose-forming amylase thus immobilized was filled in a glass column with a diameter of 27 mm and a length of 130 mm. A 26.2% (w/w) liquefied starch (DE=7, pH 7.2) was used as the substrate and was continuously passed through the glass column at a temperature of 45° C. and a space velocity of 2.0, 5.0 or b 10.0 hr$^{-1}$. The weight hourly space velocity per unit activity was $2.42 \times 10^{-3}$, $6.05 \times 10^{-3}$ or $1.21 \times 10^{-2}$ hr$^{-1}$(IU/g)$^{-1}$, respectively. The results are shown in Table 3. Changes in the maltotetraose content of the reaction mixture with a elapsed time when the liquefied starch was continuously passed through the glass column at a space velocity of 2.0 hr$^{-1}$ are shown in FIG. 2.

COMPARATIVE EXAMPLE 3

The immobilized maltotetraose-forming amylase (10 g, exhibited activity 215 IU/g) which has been obtained by immobilizing onto Duolite adsorption resin S-761 as the support in the same manner as in Example 3 was filled in a reactor. A 26.2% (w/w) liquefied starch (DE=7, pH 7.2) as the starting material was continuously passed through the reactor under conditions of 24 ml/hr, temperature 45° C. and space velocity 2.0, 5.0 or 10 hr$^{-1}$. The weight hourly space velocity per unit activity was $3.48 \times 10^{-3}$, $8.71 \times 10^{-3}$ or $1.74 \times 10^{-2}$ hr$^{-1}$, respectively. The results are shown in Table 3. Changes in the maltotetraose content of the reaction mixture with a elapsed time when the liquefied starch was continuously passed at a space velocity of 2.0 hr$^{-1}$ are shown in FIG. 2.

TABLE 3

| | Concentration of Maltotetraose in Reaction Mixture (%) | |
|---|---|---|
| Space Velocity (hr$^{-1}$) | Example 3 | Comparative Example 3 |
| 2.0 | 44.5 | 42.6 |
| 5.0 | 44.1 | 37.2 |
| 10.0 | 41.7 | 32.5 |

As described above, the present invention permits production of maltotetraose of higher purity in comparison with the prior art immobilized enzyme.

COMPARATIVE EXAMPLE 4

The immobilized maltotetraose-forming amylase (6.6 g, exhibited activity 273 IU/g) which had been obtained in the same manner as in Example 3 wa filled in a reactor. A 10% (w/w) liquefied starch (DE=8./0, pH=6.8) was continuously passed through the reactor under conditions of temperature 40° C. and flow rate 1.1 ml/hr (weight hourly space velocity per unit activity, $6.83 \times 10^{-5} hr^{-1}(IU/g)^{-1}$) to obtain a reaction product. The composition of the product is shown in Table 4.

COMPARATIVE EXAMPLE 5

The immobilized maltotetraose-forming amylase (6.6 g, exhibited activity 46.7 IU/g) which had been obtained in the same manner as in Example 3 was filled in a reactor. A 30% (w/w) liquefied starch (DE=8.0, pH 6.8) was continuously passed through the reactor under conditions of temperature 40° C. and flow rate 210 ml/hr (weight hourly space velocity per unit activity, $2.29 \times 10^{-1} hr^{-1}(IU/g)^{-1}$) to obtain a reaction product. The composition of the product is shown in Table 4.

TABLE 4

| | Composition of Reaction Product (%) | |
|---|---|---|
| | Comparative Example 4 | Comparative Example 5 |
| $G_1$ to $G_3$ *1 | 85.0 | 17.3 |
| $G_4$ *2 | 11.0 | 11.0 |
| $G_5^+$ *3 | 4.0 | 76.7 |

*1 Glucose, maltose and maltotriose
*2 Maltotetraose
*3 Maltopentaose and higher molecular weight saccharides It can be seen that if the weight hourly space velocity per unit activity is less than $1 \times 10^{-4} hr^{-1}(IU/g)^{-1}$, or more than $2 \times 10^{-1} hr^{-1}(IU/g)^{-1}$, the yield of maltotetraose is small.

EXAMPLE 4

Pullulanase (originating from *Lkebsiella pneumoniae*, specific activity 50 IU/mg-protein, produced by Amano Pharmaceutical Co., Ltd.) as the debranching enzyme was immobilized onto Chitopearl BCW 3505 in the same manner as in Example 1 except that a phosphate buffer (pH 6.0) was used. The exhibited activity of the immobilized pullulanase was 129 IU/g-support.

A mixture of 4 ml of immobilized glucoamylase and 9.0 ml of immobilized pullulanase as obtained above (exhibited activity ratio, about 3:1) was filled in two glass columns with a diameter of 10 mm and a length of 200 ml. A 30% (w/w) liquefied corn starch (DE=11, pH 5.5) was used as the substrate and continuously passed through under conditions of temperature 50° C. and space velocity 0.25, 0.5 or 1.0 $hr^{-1}$ (weight hourly space velocity per unit activity; $2.48 \times 10^{-4}$, $4.95 \times 10^{-3}$ or $9.89 \times 10^{-} hr^{-1}(IU/g)^{-1}$, respectively). The results obtained are shown in Table 5.

TABLE 5

| | Concentration of Glucose in Reaction Product (%) | |
|---|---|---|
| Space Velocity ($hr^{-1}$) | Example 4 | Example 1 |
| 0.25 | 95.8 | 95.2 |
| 0.5 | 97.3 | 96.7 |
| 1.0 | 96.1 | 95.2 |

As shown in Table 5, the concentration of glucose in the reaction mixture is increased by about 1% by using the dual immobilized enzyme system in place of the single immobilized enzyme system.

EXAMPLE 5

The immobilized β-amylase (10 ml) obtained in the same manner as in Example 2 and 10 ml of immobilized pullulanase obtained in the same manner as in Example 4 were mixed (with regard to exhibited activity ratio, β-amylase: pullulanase=2.1:1.0) and filled in. A 25.0% (w/w) liquefied starch (DE=7, pH 6.0) was used as the substrate and continuously passed through under conditions of temperature 50° C. and flow rate of 15 ml/hr (weight hourly space velocity per unit activity, $2.32 \times 10^{-3} hr^{-1}(IU/g)^{-1}$). The composition of the column effluent after the operation for 0, 15 and 30 days is shown in Table 6. As shown in the table, the dual immobilized enzyme system increases the maltose purity by about 10 to 12% in comparison with the single enzyme system using β-amylase alone, and even after 30 days, almost no decrease in activity is observed.

TABLE 6

| | Changes with Time in Amount of Maltose Formed | |
|---|---|---|
| Days | Single Enzyme System | Dual Enzyme System |
| 0 | 53.0% | 64.2% |
| 15 | 51.8% | 64.2% |
| 30 | 50.1% | 64.0% |

EXAMPLE 6

The immobilized maltotetraose-forming amylase (10 ml) obtained in the same manner as in Example 3 and 5 ml of an immobilized pullulanase obtained in the same manner as in Example 3 (exhibited activity ratio: β-amylase: pullulanase =4:1) were mixed and filled A 26.2% (w/w) liquefied starch (DE=7, pH 7.2) was used as the substrate and continuously passed under conditions of temperature 40° C. and flow rate 24 ml/hr (weight hourly space velocity per unit activity, $4.06 \times 10^{-3} hr^{-1}(IU/g)^{-1}$). The composition of the column effluent after the operation for 0, 15 or 30 days is shown in Table 7. As shown in the table, the dual enzyme system increases the maltotetraose purity by about 5% in comparison with the single enzyme system using the immobilized maltotetraose-forming amylase alone, and even after 30 days, almost no decrease in activity is observed.

TABLE 7

| | Changes with Time in Amount of Maltotetraose Formed | |
|---|---|---|
| Days | Single Enzyme System | Dual Enzyme System |
| 0 | 45.2% | 50.5% |
| 15 | 44.0% | 48.3% |
| 30 | 42.9% | 46.2% |

EXAMPLE 7

Maltotetraose-producing amylase (originating from *Pseudomonas stutzeri*, specific activity 80.8 IU/g-protein) was immobilized onto Duolite Adsorption Resin "S-761" to obtain an immobilized enzyme. That is, 20 g of the support was sufficiently equilibrated with a 50 mM Tris-HCl buffer (pH 7.0), 20,000 IU of the enzyme was added, and the resulting mixture was subjected to reciprocal shaker (120 strokes/ minute and 4 cm width in a 300 ml Erlenmeyer flask) at room temperature for 1 hour to immobilize the enzyme onto the support.

Then the mixture was filtered with a filter paper and fully washed with a 10 mM Tris-HCl buffer (pH 7.0) until no protein was eluted, to obtain an immobilized maltotetraose-forming amylase having an exhibited activity of 252 IU/g-support.

Debranching enzyme, pullulanase (originating from *Klebsiella pneumoniae*, specific activity 50 IU/mg-protein) was immobilized using the same support as used above in the same manner as above except that a phosphate buffer (pH 6.0) was used, to obtain an immobilized enzyme having an exhibited activity of 74.9 IU/g-support.

Two glass columns having a diameter of 27 mm and a length of 130 mm were used. In one column, 10 ml of the immobilized maltotetraose-forming amylase was filled, and a mixture of 10 ml of the immobilized maltotetraose-forming amylase and 8 ml of the immobilized debranching enzyme (exhibited activity ratio, former:-latter=about 4:1) was filled in the other column. A 26.2% (w/w) liquefied starch (DE=7, pH 7.2) was used as the substrate and continuously passed through under conditions of temperature 45° C. and flow rate 24 ml/hr (weight hourly space velocity per unit activity, $3.52 \times 10^{-3}$ hr$^{-1}$(IU/g)$^{-1}$). The results are shown in FIG. 3.

As apparent from FIG. 3, even if 850 hour continuous operation is performed, no decrease in activity is observed in both the columns. In the column (Column I) in which only the immobilized maltotetraose-forming amylase was filled, the amount of maltotetraose formed was about 45% (w/w), while on the other hand in the column (Column II) of the dual enzyme system in which the immobilized maltotetraose-forming amylase and the immobilized debranching enzyme were mixed, the amount of maltotetraose formed was about 50% (w/w).

EXAMPLE 8

Immobilized pullulanase was obtained using pullulanase originating from *Klebsiella pneumoniae* (specific activity 50 IU/mg-protein, produced by Amano Pharmaceutical Co., Ltd.) as the enzyme, and as the support, those shown in Table 8. That is, 0.2 g of the support and 2.0 ml of 40 IU enzyme in a 0.1 M phosphate buffer (pH 7.0) were placed in a test tube with an inner diameter of 20 mm, which was then subjected to reciprocal shaker under conditions of 120 strokes and 4 cm width at room temperature for 1 hour to immobilize the enzyme onto the support. After filtration, sufficient washing was applied using a 20 mM phosphate buffer (pH 7.0) until no protein was eluted, to obtain an immobilized pullulanase.

The exhibited activity of the above immobilized pullulanase was measured by the following method. That is, 10 mg (wet) of the immobilized pullulanase was added to 0.5 ml of a 10 mM phosphate buffer (pH 7.0) in a 50 ml Erlenmeyer flask. Then, 10 w/v% of pullulan (produced by Hayashibara Biochemical Research Institute, molecular weight $6.5 \times 10^4$) was added. The resulting mixture was reciprocated at 40° C. for 10 minutes under conditions of 120 strokes/minute and 4 cm width by the use of a reciprocating shaker to proceed the enzymatic reaction. The reducing sugar formed was measured by the Somogyi-Nelson method with maltotriose as a standard to determine exhibited activity. One unit means the amount of enzyme hydrolyzing 1 μmol of glucoside bond for one minute. The exhibited activity of the immobilized pullulanase is shown in Table 8.

EXAMPLE 9

Using pullulanase originating from *Bacillus acidopullulyticus* (specific activity 4.9 IU/mg-protein, produced by Novo Co., Ltd.) as the enzyme and as the support, those shown in Table 9, immobilized pullulanase was obtained in the same manner as in Example 8. Immobilization was performed in the same manner as in Example 8 except that in the immobilization, an acetate buffer (pH 4.5) was used. The exhibited activity of the immobilized pullulanase was measured in the same manner as in Example 8 except that the pH was adjusted to 4.5. The results obtained are shown in Table 9.

TABLE 8

| Support | Exhibited Activity (IU/g-support) |
| --- | --- |
| slightly weak acidic porous adsorption resin | |
| Duolite S-761 | 66.1 |
| Duolite S-762 | 74.9 |
| Phenol-based adsorption resin | |
| Duolite A-7 | 61.7 |
| Duolite A-562 | 66.1 |
| Duolite S-587 | 63.1 |
| Granular porous chitosan Chitopearl BCW 3505 | 135.4 |

TABLE 9

| Support | Exhibited Activity (IU/g-support) |
| --- | --- |
| slightly weak acidic porous adsorption resin | |
| Duolite S-761 | 40.3 |
| Duolite S-762 | 65.9 |
| Duolite ES-771 | 31.8 |
| Weakly acidic cationic exchange resin | 90.6 |
| Duolite C-464 | |
| Granular porous chitosan Chitopearl BCW 3505 | 140.2 |

COMPARATIVE EXAMPLE 6

Using pullulanase originating from *Klebsiella pneumoniae* (specific activity 50 IU/mg-protein, produced by Amano Pharmaceutical Co., Ltd.) as the enzyme and as the support, celite, pearlite or activated alumina shown in Table 10, immobilized pullulanase was obtained in the same manner as in Example 8. The exhibited activity of the immobilized pullulanase is shown in Table 10.

TABLE 10

| Support | Exhibited Activity (IU/g-support) |
| --- | --- |
| Celite | 22.2 |
| Pearlite | 31.5 |
| Activated alumina | 13.7 |

EXAMPLE 10

Using maltotetraose-forming amylase (originating from *Pseudomonas stutzeri*, specific activity 80.8 IU/mg-protein) as the enzyme and a slightly weak adsorption resin, Duolite S-761 (produced by Diamond Shamrock Corp.) as the support for immobilization, an immobilized enzyme was obtained. That is, 20 g of the support was sufficiently equilibrated with a 50 mM Tris-HCl buffer (pH 7.0), 20,000 IU of the enzyme dissolved in 100 ml of the same buffer as above was added, and the resulting mixture was subjected to reciprocal shaker (120 strokes/minute and 4 cm width in a 300 ml Erlenmeyer flask) at room temperature for 1 hour to immobilize the enzyme onto the support. After filtration with a filter paper, sufficient washing using a 10 mM Tris-HCl buffer (pH 7.0) was applied until no protein was eluted, to obtain an immobilized maltotetraose-forming amylase having an exhibited activity of 252 IU/g-protein.

Debranching enzyme, pullulanase (originating from *Klebsiella pneumoniae*, specific activity 50 IU/mg-protein) was immobilized onto the same support as above in the same manner as above except that a phosphate buffer (pH 6.0) was used, to obtain an immobilized enzyme having an exhibited activity of 74.9 IU/g-support.

Two glass columns each having a diameter of 27 mm and a length of 130 mm were used. In one column, 10 ml of the immobilized maltotetraose-forming amylase was filled, and a mixture of 10 ml of the immobilized maltotetraose-forming amylase and 8 ml of the immobilized debranching enzyme (about 4:1 in terms of exhibited activity ratio) was filled in the other column. A 26.2% (w/w) liquefied starch (DE=8, pH 7.2) was used as the substrate and continuously passed through at a temperature of 45° C and a flow rate of 24 ml/hr (weight hourly space velocity per unit activity, $3.52 \times 10^{-3}$ $hr^{-1}(IU/g)^{-1}$). The results are shown in Table 11. Changes with time in the concentration of maltotetraose in the column effluent in the single enzyme system and the dual enzyme system when the liquefied starch was continuously passed through under the above conditions are shown in Table 12.

EXAMPLE 11

Using granular porous chitosan, Chitopearl BCW 3505 (produced by Fuji Boseki Co., Ltd.) as the support, maltotetraose-forming amylase and pullulanase were immobilized according to the method described in Example 10. The exhibited activities of the immobilized maltotetraose-forming amylase and the immobilized pullulanase were 350 IU/g-support and 112 IU/g-support, respectively In a glass column with a diameter of 27 mm and a length of 130 mm, a mixture of 10 ml of the immobilized maltotetraose-forming amylase and 5 ml of the immobilized pullulanase (about 4:1 in terms of exhibited activity ratio). A 26.2% (w/w) liquefied starch (DE=8, pH 7.2) was used as the substrate and continuously passed through under conditions of temperature 45° C. and flow rate 30 ml/hr (weight hourly space velocity per unit activity, $3.19 \times 10^{-3}$ $hr^{-1}(IU/g)^{-1}$). The results are shown in Table 11. Changes with time in the concentration of maltotetraose in the column effluent in the single enzyme system and the dual enzyme system when the liquefied starch was passed through under the above conditions are shown in Table 12.

TABLE 11

| Example | Maltotetraose Purity of Column Effluent (%) | | Single Enzyme System (Maltotetraose-forming amylase) | Dual Enzyme System (Maltotetraose-forming amylase + Debranching enzyme) |
|---|---|---|---|---|
| | Enzyme | Support | | |
| 10 | Maltotetraose-forming amylase | Duolite S-761 | 44.8 | 50.3 |
| | Debranching enzyme | Duolite S-761 | | |
| 11 | Maltotetraose-forming enzyme | Chitopearl BCW 3505 | 45.2 | 50.9 |
| | Debranching enzyme | Chitopearl BCW 3505 | | |

TABLE 12

Changes with Time in Concentration of Maltotetraose in Column Effluent (%)

| Example | Reaction Time (days) | Single Enzyme System | Dual Enzyme System |
|---|---|---|---|
| 10 | 0 | 44.8 | 50.3 |
| | 10 | 41.5 | 49.2 |
| | 20 | 40.0 | 47.8 |
| | 30 | 39.1 | 46.0 |
| 11 | 0 | 45.2 | 50.9 |
| | 10 | 45.0 | 50.0 |
| | 20 | 44.5 | 49.0 |
| | 30 | 43.9 | 48.2 |

EXAMPLE 12

Glucoamylase originating from *Rhizopus delemar* (produced by Shin Nippon Kagaku Co., Ltd.) was immobilized onto a slightly weak acidic adsorption resin, Duolite S-761 (produced by Diamond Shamrock Corp.) as the support. That is, chitosan as the support was sufficiently equilibrated with a 20 mM acetate buffer (pH 5.5). Chitosan (10 g, wet) was placed into a 100 ml Erlenmeyer flask, and 10,500 units of glucoamylase was added (1,050 units per gram of the support). The resulting mixture was subjected to reciprocal shaker (120 strokes/minute) at room temperature for 1 hour to achieve immobilization. Washing was performed sufficiently with a 20 mM acetate buffer (pH 5.0) to obtain an immobilized glucoamylase sample. The exhibited activity of the immobilized glucoamylase thus obtained was 368 IU/g-support.

Debranching enzyme, pullulanase (originating from *Klebsiella pneumoniae*, specific activity 50 IU/mg-protein) was immobilized onto the same support as above in the same manner as above except that a phosphate buffer (pH 6.0) was used, to obtain an immobilized enzyme having an exhibited activity of 73.2 IU/g-support.

In one of two glass columns having a diameter of 10 mm and a length of 150 mm, 5 ml of the immobilized glucoamylase was filled, and a mixture of 5 ml of the immobilized glucoamylase and 5 ml of the immobilized pullulanase (exhibited activity ratio, about 5:1) was filled in the other glass column. A 30.3% (w/w) liquefied corn starch (DE=11, pH 5.5) was used as the substrate and continuously passed through the glass column under conditions of temperature 50° C and flow rate of 3.5 ml/hr (weight hourly space velocity per unit activity, $8.28 \times 10^{-4}$ $hr^{-1}(IU/g)^{-1}$). The results are shown in Table 13.

EXAMPLE 13

Granular porous chitosan, Chitopearl BCW 3505 (produced by Fuji Spinning Co., Ltd.) was used as the support, and glucoamylase and pullulanase were immobilized thereonto in the same manner as in Example 12.

The exhibited activities of the immobilized glucoamylase and the immobilized pullulanase were 435 IU/g-support and 112 IU/g-support, respectively.

In one of two glass columns having a diameter of 10 mm and a length of 150 mm, 5 ml of the immobilized glucoamylase was filled, and a mixture of 5 ml of the immobilized glucoamylase and 5 ml of the immobilized pullulanase (exhibited activity ratio, about 4:1) was filled in the other column. A 30.3% (w/w) liquefied corn starch (DE=11, pH 5.5) was used as the substrate and continuously passed through the glass column under conditions of temperature 50° C. and flow rate of 3.3 ml/hr (weight hourly space velocity per unit activity, $6.60 \times 10^{-4}$ hr$^{-1}$(IU/g)$^{-1}$). The results are shown in Table 13. Following the same method as above except that the reaction temperature was changed to 45° C., the liquid was continuously passed through while changing the flow rate so that the concentration of glucose in the column effluent was not less than 95%.

The changes with time in the flow rate in the above case are shown in Table 14. Space velocity is defined by the following equation.

$$\text{Space Velocity (hr}^{-1}) = \frac{\text{Flow Rate (ml/hr)}}{\text{Bed Volume (ml)}}$$

TABLE 13

| Example | Glucose Purity of Column Effluent (%) | | Single Enzyme System (Glucoamylase) | Dual Enzyme System (Glucoamylase + Debranching Enzyme) |
|---|---|---|---|---|
| | Enzyme | Support | | |
| 12 | Gluocoamylase | Duolite S-761 | 94.7 | 97.0 |
| | Debranching Enzyme | Duolite S-761 | | |
| 13 | Glucoamylase | Chitopearl BCW 3505 | 97.2 | 97.7 |
| | Debranching Enzyme | Chitopearl BCW 3505 | | |

TABLE 14

| | | Changes with Time in Flow Rate | | | |
|---|---|---|---|---|---|
| | | Single Enzyme System | | Dual Enzyme System | |
| Example | Reaction Time (days) | Space Velocity (hr$^{-1}$) | Glucose Purity (%) | Space Velocity (hr$^{-1}$) | Glucose Purity (%) |
| 13 | 0 | 0.72 | 96.2 | 0.81 | 97.4 |
| | 10 | 0.51 | 95.4 | 0.57 | 96.2 |
| | 20 | 0.40 | 96.1 | 0.51 | 96.3 |
| | 30 | 0.37 | 95.5 | 0.47 | 95.9 |

EXAMPLE 14

A slightly weak acidic adsorption resin, Duolite S-761 (produced by Diamond Shamrock Corp.), was used as the support, and β-amylase (originating from soybean, produced by Nagase Seikagaku Kogyo Co., Ltd.) was immobilized thereonto by the usual method. The exhibited activity of the immobilized β-amylase was 215 IU/g-support.

In one of two glass columns having a diameter of 10 mm and a length of 150 ml, 5 ml of the immobilized β-amylase was filled, and a mixture of 5 ml of the immobilized β-amylase and 4.0 ml of the immobilized pullulanase (exhibited activity, 4.9 IU/g-support) as obtained by the method described in Example 4 (exhibited activity ratio, about 4:1) was filled in the other column. A 25% (w/w) liquefied starch (DE=8, pH 6.0) was used as the substrate and continuously passed through the column under conditions of temperature 50° C. and flow rate 5.2 ml/hr (weight hourly space velocity per unit activity, $1.71 \times 10^{-3}$ hr$^{-1}$(IU/g)$^{-1}$). The results are shown in Table 15.

EXAMPLE 15

Porous chitosan, Chitopearl BCW 3505 (produced by Fuji Spinning Co., Ltd.), was used as the support, and β-amylase (originating from soybean, produced by Nagase Seikagaku Kogyo Co., Ltd.) was immobilized thereonto by the usual method. The exhibited activity of the immobilized β-amylase was 301 IU/g-support.

Pullulanase originating from *Klebsiella pneumoniae* was immobilized onto the same support as above by the method described in Example 3. The exhibited activity of the enzyme thus immobilized was 112 IU/g-support.

In one of two glass columns having a diameter of 10 mm and a length of 150 mm, 5 ml of the immobilized β-amylase was filled, and a mixture of 5 ml of the immobilized β-amylase and 2.5 ml of the immobilized pullulanase (exhibited activity ratio, about 4:1) was filled in the other column. A 25% (w/w) liquefied starch (DE=8, pH 6.0) was used as the substrate and continuously passed through the glass column under conditions of temperature 50° C. and flow rate 4.9 ml/hr (weight hourly space velocity per unit activity, $1.5 \times 10^{-3}$ hr$^{-1}$(IU/g)$^{-1}$). The results are shown in Table 15.

Changes with time in the concentration of maltose in the column effluent in the single enzyme system and the composite enzyme system when the liquefied starch was passed through the column under the conditions as described above are shown in Table 16.

TABLE 15

| | Maltose Purity of Column Effluent (%) | | | |
|---|---|---|---|---|
| Example | Enzyme | Support | Single Enzyme System (β-Amylase) | Dual Enzyme System (β-Amylase + Debranching Enzyme) |
| 14 | β-Amylase | Duolite S-761 | 52.4 | 63.8 |
| | Debranching Enzyme | Duolite S-761 | | |
| 15 | β-Amylase | Chitopearl BCW 3505 | 53.2 | 64.5 |
| | Debranching Enzyme | Chitopearl BCW 3505 | | |

TABLE 16

| | Maltose Purity of Column Effluent (%) | | |
|---|---|---|---|
| Example | Reaction Time (days) | Single Enzyme System | Dual Enzyme System |
| 15 | 0 | 53.2 | 64.5 |
| | 10 | 53.0 | 65.0 |
| | 20 | 52.0 | 64.2 |
| | 30 | 51.2 | 63.9 |

The immobilized debranching enzyme of the present invention can be used efficiently. Furthermore when used in combination with various amylases, the immobilized debranching enzyme of the present invention can increase the yield of the objective starch sugar. In particular, when the immobilized debranching enzyme of the present invention is used in combination with various immobilized amylases, various starch sugars can be produced in high yield by continuous operation.

What is claimed is:

1. A process for producing starch sugar which comprises contacting liquefied starch with amylase immobilized on porous beads of chitosan produced by deacetylating natural polymer chitin and crosslinking with a crosslinking agent to impact acid resistance, and further introducing an aliphatic or aromatic functional group as a spacer.

2. The process as claimed in claim 1 wherein the amylase is glucoamylase, β-amylase or maltooligosaccharide-forming amylase.

3. The process of claim 1 wherein the beads of chitosan have a diameter of 0.1 to 3 mm, a pore diameter of not more than 3 μm and a specific surface area of 15 to 230 m²/g.

4. The process of claim 3 wherein the crosslinking is with dicarboxylic acid, dialdehyde or diisocyanate.

5. A process for producing starch sugar which comprises contacting liquefied starch with a combination of amylase and a debranching enzyme, both immobilized on porous beads of chitosan produced by deacytalating natural polymer chitin and crosslinking with a crosslinking agent to impart acid resistance, and further introducing an aliphatic or aromatic functional group as a spacer.

6. The process as claimed in claim 5 wherein the amylase is glucoamylase, β-amylase or maltooligosaccharide-forming amylase.

* * * * *